United States Patent
Standke et al.

(10) Patent No.: US 7,834,073 B2
(45) Date of Patent: Nov. 16, 2010

(54) STABLE SOLUTIONS OF N-SUBSTITUTED AMINOPOLYSILOXANES, THEIR PREPARATION AND USE

(75) Inventors: Burkhard Standke, Loerrach (DE); Peter Jenkner, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 284 days.

(21) Appl. No.: 11/569,363

(22) PCT Filed: May 12, 2005

(86) PCT No.: PCT/EP2005/052168

§ 371 (c)(1), (2), (4) Date: Nov. 20, 2006

(87) PCT Pub. No.: WO2005/118599

PCT Pub. Date: Dec. 15, 2005

(65) Prior Publication Data

US 2008/0003448 A1     Jan. 3, 2008

(30) Foreign Application Priority Data

May 26, 2004 (DE) .................. 10 2004 025 767

(51) Int. Cl.
*C08K 5/54* (2006.01)

(52) U.S. Cl. ............... 524/262; 524/267; 524/379; 528/26; 528/38; 428/428; 428/429; 428/447; 428/448; 428/450

(58) Field of Classification Search ............... 556/413, 556/401, 425; 528/38, 26; 524/379, 386, 524/389; 525/418–420
See application file for complete search history.

(56) References Cited

U.S. PATENT DOCUMENTS

| | | | |
|---|---|---|---|
| 4,226,793 A | 10/1980 | Kotzsch et al. |
| 5,591,818 A | 1/1997 | Standke et al. |
| 5,629,400 A | 5/1997 | Standke et al. |
| 5,679,147 A | 10/1997 | Standke et al. |
| 5,808,125 A | 9/1998 | Standke et al. |
| 5,817,854 A | 10/1998 | Horn et al. |
| 5,849,942 A | 12/1998 | Standke et al. |
| 5,863,509 A | 1/1999 | Standke et al. |
| 5,885,341 A | 3/1999 | Standke et al. |
| 5,932,757 A | 8/1999 | Standke et al. |
| 6,054,601 A | 4/2000 | Standke et al. |
| 6,118,015 A | 9/2000 | Haas et al. |
| 6,133,466 A | 10/2000 | Edelmann et al. |
| 6,139,622 A | 10/2000 | Gobel et al. |
| 6,176,918 B1 | 1/2001 | Glausch et al. |
| 6,177,582 B1 | 1/2001 | Jenkner et al. |
| 6,228,936 B1 | 5/2001 | Standke et al. |
| 6,239,194 B1 | 5/2001 | Standke et al. |
| 6,251,989 B1 | 6/2001 | Edelmann et al. |
| 6,255,513 B1 | 7/2001 | Standke et al. |
| 6,255,516 B1 | 7/2001 | Jenkner et al. |
| 6,288,256 B1 | 9/2001 | Standke et al. |
| 6,361,871 B1 | 3/2002 | Jenkner et al. |
| 6,395,858 B1 | 5/2002 | Mack et al. |
| 6,403,228 B1 | 6/2002 | Mack et al. |
| 6,426,150 B1 | 7/2002 | Jenkner et al. |
| 6,491,838 B1 | 12/2002 | Standke et al. |
| 6,500,883 B1 | 12/2002 | Mack et al. |
| 6,534,667 B1 | 3/2003 | Standke et al. |
| 6,641,870 B2 | 11/2003 | Bartkowiak et al. |
| 6,685,766 B2 | 2/2004 | Standke et al. |
| 6,713,186 B1 | 3/2004 | Jenkner et al. |
| 6,767,982 B2 | 7/2004 | Standke et al. |
| 6,770,327 B2 | 8/2004 | Edelmann et al. |
| 6,841,197 B2 | 1/2005 | Standke et al. |
| 7,611,753 B2 | 11/2009 | Bartkowiak et al. |
| 2002/0127415 A1 | 9/2002 | Standke et al. |
| 2002/0192385 A1 | 12/2002 | Jenkner et al. |
| 2004/0138355 A1 | 7/2004 | Saito et al. |
| 2006/0185555 A1 | 8/2006 | Giessler et al. |
| 2008/0058489 A1 | 3/2008 | Edelmann et al. |
| 2008/0210130 A1 | 9/2008 | Giessler-Blank et al. |
| 2009/0011246 A1 | 1/2009 | Giessler-Blank et al. |
| 2009/0022898 A1 | 1/2009 | Standke et al. |

OTHER PUBLICATIONS

Feher, Frank J. et al.,"Amine and Ester-Substituted Silsesquioxanes: Synthesis, Characterization and Use as a Core for Starburst Dendrimers", Chem. Commun., No. 3, pp. 323-324, 1998.
Feher Frank J. et al., Octafunctionalized Polyhedral Ologosilsesquioxanes as Scaffolds: Synthesis of Peptidyl Silsesquioxanes, Chem. Commun., No. 14, pp. 1469-1470, 1998.
Feher, Frank J. et al.,"Syntheses of Highly Functionalized Cube-Octameric Polyhedral Oligosilsesquioxanes $(R_8Si_8O_{12})$", J. Chem. Soc., Dalton Trans., No. 9, pp. 1491-1497, 1999.
U.S. Appl. No. 08/124,955, filed Sep. 21, 1993, Standke et al.
U.S. Appl. No. 11/572,555, filed Jan. 23, 2007, Just, et al.
U.S. Appl. No. 10/581,690, filed Jun. 6, 2006, Standke.
U.S. Appl. No. 11/576,504, filed Apr. 2, 2007, Mueh, et al.
U.S. Appl. No. 11/718,442, filed May 2, 2007, Standke.
U.S. Appl. No. 11/815,391, filed Aug. 2, 2007, Standke, et al.
U.S. Appl. No. 11/814,127, filed Jul. 17, 2007, Standke, et al.
U.S. Appl. No. 12/161,112, filed Jul. 16, 2008, Standke, et al.
U.S. Appl. No. 12/596,725, filed Oct. 20, 2009, Giessler-Blank, et al.
U.S. Appl. No. 12/673,390, filed Feb. 16, 2010, Wassmer, et al.

*Primary Examiner*—Marc S Zimmer
(74) *Attorney, Agent, or Firm*—Oblon, Spivak, McClelland, Maier & Neustadt, L.L.P.

(57) ABSTRACT

Stable low chloride solutions of hydrosalts of an organic acid with a N-substituted aminopolysiloxane in the form of a T structural unit contain at least one lower alcohol, and at least one stabilizer. Methods to prepare the stable low-chloride solutions are also provided.

17 Claims, No Drawings

STABLE SOLUTIONS OF N-SUBSTITUTED AMINOPOLYSILOXANES, THEIR PREPARATION AND USE

CROSS REFERENCE TO RELATED APPLICATIONS

This application is the National Stage of PCT/EP05/052168, filed May 12, 2005. The parent application claims priority to German Application No. 10 2004-025 767.1 filed May 26, 2004. The disclosures of both applications are incorporated herein by reference in their entireties.

BACKGROUND OF THE INVENTION

The present invention relates to stable, low-chloride solutions of hydrosalts of organic acids with cationic N-substituted aminopolysiloxanes, present substantially in the form of T structural units, in a lower alcohol, to the preparation of these solutions, and to their use as adhesion promoters and for coating various substrate materials.

Solutions of organosilane polycondensates and their preparation and use are described in a host of publications.

The promotion of adhesion by functionalized aminopropyltrimethoxysilanes in the coating of metals, copper and iron for example, with polyolefins or epoxy resins is reported in U.S. Pat. No. 4,902,556, EP-A-0 353 766 and U.S. Pat. No. 4,849,294. Adhesion is promoted on glass surfaces in accordance with EP-A-0 338 128, WO 88/00527, U.S. Pat. No. 4,499,152, U.S. Pat. No. 4,382,991, U.S. Pat. No. 4,330,444, DE-A-28 02 242 and EP-A-0 845 040. Adhesion promoters for oxidic fillers in various organic polymers are described in JP-A-01/259369 and EP-A-0 176 062.

Aqueous formulations of such substances with low concentrations of active substance, below 1%, are described in JP-A-62/243624, U.S. Pat. No. 4,499,152, U.S. Pat. No. 4,382,991, U.S. Pat. No. 4,330,444 and DE-A-28 02 242.

DE-A-26 48 240 describes water-soluble silylalkylamine chlorides which are suitable for use as coupling agents between inorganic substrates.

U.S. Pat. No. 5,591,818 and EP-A-0 590 270 disclose organosilanes and their poly-condensation products, which are prepared by hydrolyzing a functional aminosilane hydrosalt or by hydrolytically polymerizing an aminosilane with subsequent functionalization by reaction with a functional alkyl halide. The compounds can be formulated as stable aqueous emulsions and used as adhesion promoters between organic and inorganic materials.

U.S. Pat. No. 5,073,195 discloses compositions for treating porous surfaces to make them water repellent, these compositions being aqueous solutions of a silane coupling agent and an alkyltrialkoxysilane having $C_1$-$C_6$ alkyl groups on the silicon atom. The solutions are used for treating substrate materials such as wood, concrete, lime sandstone or other unreactive surfaces of building materials.

EP-A-0 538 551 is directed to emulsions which contain organosilicon compounds and are intended for impregnating inorganic materials, especially building materials. The emulsions comprise water, at least one alkoxysilane with or without oligomers thereof, one or more anionic surfactants, and also silicon-functional surfactants and customary auxiliaries. The surfactant group is introduced into alkylalkoxysilanes in the form of the hydrochloride salt by reaction with the surfactant radical, in the form of the Na alkoxide, in an organic solvent. Stable emulsions are obtained by using high-pressure homogenizers with two passes at pressures of from 8 to 50 MPa and from 10 to 70 MPa, the pressure reduction in the second pressure stage amounting to 20%. Droplet sizes <1 µm are obtained.

At the 39th annual conference of the Institut für verstarkte Kunststoffe/Verbundwerkstoffe [Institute for Reinforced Plastics/Composites] of the Gesellschaft der Kunststoffindustrie [German Plastics Industry Association] from Jan. 16 through 19, 1984, E. P. Plueddemann reported on silanols and siloxanes as coupling agents and primers.

In U.S. Pat. No. 3,734,763 Plueddemann describes cationic unsaturated amino-functional silane coupling agents. $(CH_3O)_3Si(CH_2)_3NHCH_2CH_2NH_2$ and $(CH_3O)_3Si(CH_2)_3NHCH_2CH_2NHCH_2C_6H_4$—$CH=CH_2$ were subjected to controlled hydrolysis. The hydrolysate may undergo partial condensation. The patent describes the reaction of numerous organofunctional amines and aminosilanes with organofunctional alkyl halides in organic solvents. The products can be used as adhesion promoters between organic and inorganic surfaces and also as primers.

DETAILED DESCRIPTION OF THE PREFERRED EMBODIMENTS

This object is achieved by means of a stable solution comprising:

at least one lower alcohol;
at least one stabilizer; and
at least one hydrosalt of an organic acid with a N-substituted aminopolysiloxane comprising a T structural unit of the formula:

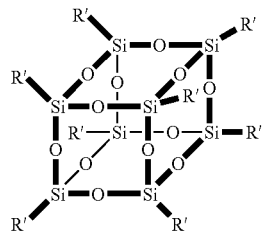

wherein
the R' groups are independently of each other, represented by formulae (Ia), (Ib), (Ic) or (Id):

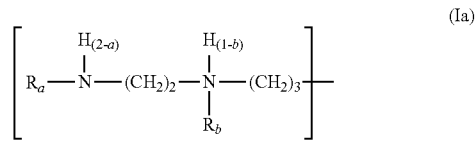

wherein a is 0, 1 or 2, and b is 0 or 1;

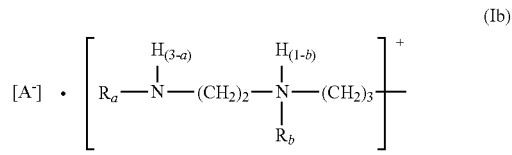

wherein a is 0, 1, 2, or 3, and b is 0 or 1;

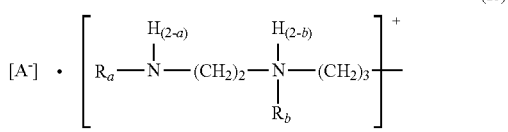

wherein a is 0, 1, or 2, and b is 0 or 1;

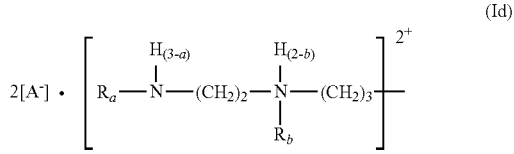

wherein a is 0, 1, 2, or 3, and b is 0, 1, or 2; and wherein the R groups independently of each other are benzyl or vinylbenzyl, A is an anion of the organic carboxylic acid, and a ratio of R' having formulae (Ib), (Ic) and (Id) to total R' is at least 0.125, a % by weight of chloride based on the total weight of the solution is less than 1%.

The at least one stabilizer is selected from the group consisting of 3,5-di-tert-butylcatechol, 2,5-di-tert-butylhydroquinone, 4-tert-butylpyrocatechol, 2,4-di-tert-butylphenol, hydroquinone monomethyl ether, 2,6-di-tert-butyl-p-cresol and a mixture thereof.

The object is also achieved by a process to prepare the above described stable solution by (i) reacting a hydrochloride salt of a N-substituted aminopolysiloxane to be obtained as a hydrosalt of an organic acid with NaOH, in solution in a lower alcohol, to obtain the N-substituted aminopolysiloxane as a free amine; separating off precipitated NaCl; and reacting the obtained free amine with the organic acid A;

or (ii) reacting a hydrochloride salt of a N-substituted aminopolysiloxane to be obtained as a hydrosalt of an organic acid, in solution in the lower alcohol, with a sodium salt of the organic acid A; and separating off precipitated NaCl;

or (iii) reacting a hydrochloride salt of a N-substituted aminopolysiloxane to be obtained as a hydrosalt of an organic acid, in solution in the lower alcohol, with a sodium alkoxide of the lower alcohol, to obtain the N-substituted aminopolysiloxane as a free amine;

separating off precipitated NaCl; and reacting the resultant free amine with the organic acid A;

and recovering a solution of the hydrosalt of the organic acid A of the N-substituted aminopolysiloxane in the lower alcohol.

The solutions contain <1.0% by weight, preferably <0.5% by weight, of chloride, based on the total weight of the solution.

The amount of cationic N-substituted aminopolysiloxanes in the solutions can be from 0.1 to 80% by weight, preferably from 30% to 60%, more preferably 40% to 50% by weight, based on the total weight of the solution.

A solution according to the invention may further have an alcohol content of from 14% to 99.9% by weight, preferably from 19% to 99.8% by weight, based on the total weight of the solution.

The components or constituents of a solution here in each case total 100% by weight.

The concentration can be adjusted by removing or adding lower alcohol.

The structure of the compounds of the invention is complex, since they comprise mixtures of siloxanes with T structure and also, where appropriate, with different N substitution.

The degree of oligomerization [x, cf. formula (I)] of the cationic N-substituted amino-polysiloxanes is generally $\geq 2$, in particular between 3 and 20. Three-dimensional structures, such as pyramids or cubes, with degrees of oligomerization of 6, 8, 10 and 12 are particularly preferred; however, corresponding transition forms may also occur and be found.

The products generally contain more than 90% of such T structural units. This is apparent from $^{29}Si$ NMR spectroscopic analyses.

The distribution of the substituents on the aminic nitrogen atoms can be determined by means of GC/MS analyses.

Surprisingly it has additionally been found that the benzyl group tends toward three-fold substitution but that disubstituted products, with substitution on the primary and secondary amino group, also occur. In the case of substitution with the vinylbenzyl group no threefold substitution was found.

Through the choice of the substituents R and the selected reaction partners and reaction conditions (temperature, reaction time, and pH) during the preparation of the cationic aminopolysiloxanes it is possible to control the distribution of the substituents on the available nitrogen atoms and to ensure that substitution takes place not only terminally on the primary amino groups but also on the secondary amino groups.

The preparation of hydrochloride salts of functionalized aminopolysiloxanes by hydrolytic polymerization of an appropriately functionalized aminosilane hydrohalide by hydrolytic polymerization or by hydrolytic polymerization of an aminosilane and subsequent functionalization by reaction of a functional alkyl halide to form oligomeric and polymeric siloxanes is described in EP-A-0 590 270.

In order to ensure substitution on secondary nitrogen atoms, controlled oligomerization is carried out of the organosilane monomer with water, the reaction taking place at elevated temperature, by means of active heating, over a time of at least 2 hours. Suitable stabilizers are used specifically in defined concentrations. This is followed by reaction with sodium methoxide and subsequent neutralization with acid.

The organic acid (A) for forming the hydrosalts is selected from, for example, formic acid, acetic acid, propionic acid, citric acid, oxalic acid, lactic acid and mixtures thereof. Acetic acid is particularly preferred.

A solution according to the invention preferably has a pH of less than 10, more preferably a pH of from 6 to 9.

The lower alcohol used even when preparing the hydrochloride salts is preferably also used as solvent for preparing the hydrosalts of organic carboxylic acids according to the invention.

The lower alcohol is selected from methanol, ethanol, isopropanol, n-propanol, isobutanol, n-butanol and t-butanol and mixtures thereof.

In addition to the stabilization of the cationic N-substituted aminopolysiloxanes by formation of a hydrosalt with an organic carboxylic acid it is possible with advantage to use further stabilizers in amounts of from 0.01% to 6%, preferably from 0.05% to 4%, more preferably from 0.1% to 1% by weight, based on the total weight of the solution.

Examples of suitable stabilizers include 3,5-di-tert-butyl-catechol, 2,5-di-tert-butyl-hydroquinone, 4-tert-butylpyrocatechol, 2,4-di-tert-butylphenol, hydroquinone mono-methyl ether, and 2,6-di-tert-butyl-p-cresol.

The stabilized solutions according to the invention are suitable with advantage for coating different substrate materials, where appropriate following dilution with water.

Thus, for example, from 0.1 to 100 parts by weight, preferably from 2 to 20 parts by weight, of a solution according to the invention, with an active substance content of about 40% by weight in particular, can be mixed with 300 parts by weights of water, the mixture giving rise, advantageously within less than 2 minutes, to a clear preparation which is ready for application.

Substrate materials used may be glass, glass fibers, metals and their oxides, such as aluminum, copper and steel, galvanized surfaces, titanium, zirconium, mixed oxides of titanium and zirconium, silicon, inorganic fillers, such as $Al(OH)_3$, $Mg(OH)_2$, mica, $Al_2O_3$, and synthetic polymers, especially polar and functional polymers, such as polyamide and polyesters, and polar polymers, such as polyolefins, which where appropriate may have been functionalized by physical pretreatment, and natural substances which have corresponding functional groups, such as paper, cotton, silk and leather.

The solutions of cationic N-substituted aminopolysiloxanes according to the invention can be used as adhesion promoters between organic and inorganic surfaces. They can also be used in connection with the reinforcement of organic polymers with inorganic fillers, glass fibers or metallic particles or in connection with the reinforcement of organic polymers with inorganic oxidic fillers. They also find use in the coating of inorganic surfaces with organic polymers or in the coating of metal, metal oxides or glass with organic polymers.

Entirely surprisingly it has been found that the T structures break up on application to substrate materials and produce a substantially more homogeneous, and thicker, coat than coats applied from monomeric functionalized silanes.

When using monomeric silanes it is possible to obtain coats of only from 10 to 50 nm, preferably about 20 nm. With the oligomeric aminopolysiloxanes according to the invention, however, coat thicknesses of up to 800 nm, in particular from 20 to 200 nm, are possible.

The coat thicknesses can be determined from the time taken for the coat to wear away under cathode ray atomization.

Without being tied to any one theory it is assumed that a coat is formed from a network in which the organic radicals R have undergone upward orientation and accumulation at the surface of the coat.

This concentration gradient can be determined by means of Auger spectroscopy, measuring the elements Si, O and C.

The invention is illustrated with reference to the following examples, without restriction of its subject-matter.

EXAMPLES

The examples are carried out using 4-necked flasks with a capacity of 1 liter or 2 liters, respectively, fitted in each case with an intensive condenser, stirrer, dropping funnel, thermometer, temperature-regulated oil bath, nitrogen atmosphere, ice-bath cooling and pressure filters or suction filters.

Example 1

Preparation of essentially N'-aminoethyl-N-vinyl-benzyl-N-aminopropylpolysiloxane hydroacetate 145 g of N'-aminoethyl-N-aminopropyltrimethoxysilane and 84.7 g of methanol are mixed. Subsequently 17.5 g of water are added. The reaction mixture is thereafter stirred for 1 hour. The oil bath is set to a temperature of 50° C. When this temperature has been reached 99.5 g of vinylbenzyl chloride are metered in over the course of one hour. The liquid phase reaches a temperature of 64° C. The subsequent reaction time amounts to 2 hours. Subsequently 120.3 g of a 30% strength by weight solution of sodium methoxide in methanol are added rapidly dropwise. The reaction mixture is cooled by means of an ice bath during this dropwise addition. The resultant sodium chloride salt is filtered off on a pressure suction filter. The NaCl is washed with 52 g of methanol. The methanol used for rinsing is combined with the filtrate and stabilized and neutralized with 0.5 g of 4-(tert-butyl)pyrocatechol in solution in 39 g of acetic acid. This gives 500 g of product solution in methanol (100% of theory). 58.5 g of NaCl are isolated. The practical yield of target product amounts to 440 g (88%). Losses arise as a result of contamination of the separated salt.

| Physical data: | pH 7.0 | Flash point approx. 11° C. |
|---|---|---|
| Si content 3.5% by weight | Density 0.94 g/ml | |
| N content 3.4% by weight | Viscosity 19 mPa s | |
| Hydrol. chloride 0.34% by weight | | |

Example 2

Preparation of essentially N'-aminoethyl-N-vinyl-benzyl-N-aminopropylpolysiloxane hydroacetate 312 g of N'-aminoethyl-N-aminopropyltrimethoxysilane and 158 g of methanol are mixed. Subsequently 158 g of water are added. The reaction mixture is thereafter stirred for 1 hour. The oil bath is set to a temperature of 50° C. When this temperature has been reached 177 g of vinylbenzyl chloride are metered in over the course of one hour. The liquid phase reaches a temperature of 64° C. The subsequent reaction time amounts to 2 hours. Subsequently 252 g of a 30% strength by weight solution of sodium methoxide in methanol are added rapidly dropwise. The reaction mixture is cooled by means of an ice bath during this dropwise addition. The resultant sodium chloride salt is filtered off on a pressure suction filter. The NaCl is washed with 104 g of methanol. The methanol used for rinsing is combined with the filtrate and stabilized and neutralized with 0.25 g of 2,6-di-tert-butyl-p-cresol in solution in 88 g of acetic acid. This gives 1000 g of product solution in methanol (100% of theory). 129 g of NaCl are isolated. The practical yield of target product amounts to 940 g (94%). Losses arise as a result of contamination of the separated salt.

| Physical data: | pH 7.0 | Flash point approx. 10° C. |
|---|---|---|
| Si content 3.7% by weight | Density 0.944 g/ml | |
| N content 3.7% by weight | Viscosity 11 mPa s | |
| Hydrol. chloride 0.30% by weight | | |

What is claimed is:

1. A stable solution comprising:
   at least one lower alcohol;
   at least one stabilizer; and
   at least one hydrosalt of an organic acid with a N-substituted aminopolysiloxane of formula (I)

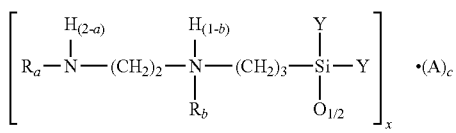

wherein
   each R is independently benzyl or vinylbenzyl,
   each Y is independently alkoxy, hydroxyl or $O_{1/2}$,
   A is an organic carboxylic acid,
   a is 0, 1 or 2,
   b is 0 or 1,
   c is greater than or equal to 0.125,
   (a+b) is from 0.125 to 3, and
   x is equal to or greater than 2; and
   the at least one hydrosalt of an organic acid with a N-substituted aminopolysiloxane of formula (I) comprises a T structural unit of the formula:

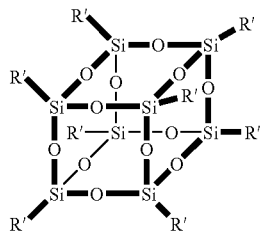

wherein
   R' is $[R_a\text{-NH}_{(2-a)}(CH_2)_2NH_{(1-b)}Rb\text{—}(CH_2)_3\text{-}]$ or is of formula (II), with the proviso that at least one of the R' groups is of formula (II):

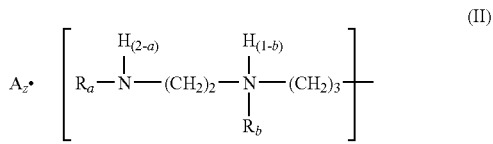

wherein
   $z \geq 1$,
   a is 0, 1 or 2, and
   b is 0 or 1;
   a % by weight of chloride based on the total weight of the solution is less than 1%, and
   the at least one stabilizer is selected from the group consisting of 3,5-di-tert-butylcatechol, 2,5-di-tert-butylhydroquinone, 4-tert-butylpyrocatechol, 2,4-di-tert-butylphenol, hydroquinone monomethyl ether, 2,6-di-tert-butyl-p-cresol and a mixture thereof.

2. The stable solution as claimed in claim 1, wherein the organic carboxylic acid A is selected from the group consisting of formic acid, acetic acid, propionic acid, citric acid, oxalic acid, lactic acid and mixtures thereof.

3. The stable solution as claimed in claim 1, wherein the lower alcohol is selected from the group consisting of methanol, ethanol, isopropanol, n-propanol, isobutanol, n-butanol, t-butanol and mixtures thereof.

4. The stable solution as claimed in claim 1, wherein an amount of the at least one hydrosalt of an organic acid with a N-substituted aminopolysiloxane is from 0.1% to 80% by weight, based on the total weight of the solution.

5. The stable solution as claimed in claim 1, wherein the amount of chloride is <0.5% by weight, based on the total weight of the solution.

6. The stable solution as claimed in claim 1, wherein an amount of alcohol is from 14% to 99.9% by weight, based on the total weight of the solution.

7. The stable solution as claimed in claim 1, wherein a pH is less than 10.

8. An adhesion promoter between organic and inorganic surfaces, comprising the stable solution of claim 1.

9. An organic polymer comprising:
   inorganic fillers, glass fibers or metallic particles and
   the stable solution of claim 1 as materials for reinforcement.

10. The organic polymer of claim 9, wherein the polymer is reinforced with inorganic oxidic fillers.

11. An inorganic surface coated with an organic polymer and the stable solution of claim 1.

12. The coated inorganic surface in claim 11 wherein the inorganic surface is metal, metal oxides or glass.

13. The coated inorganic surface in claim 11, wherein a thickness of the coating is in the range of from greater than 20 to 800 nm.

14. A process for preparing the stable solution according to claim 1, comprising:
   (i) reacting a hydrochloride salt of a N-substituted aminopolysiloxane to be obtained as a hydrosalt of an organic acid with NaOH, in solution in a lower alcohol, to obtain the N-substituted aminopolysiloxane as a free amine;
   separating off precipitated NaCl; and
   reacting the obtained free amine with the organic acid A;
   or
   (ii) reacting a hydrochloride salt of a N-substituted aminopolysiloxane to be obtained as a hydrosalt of an organic acid, in solution in the lower alcohol, with a sodium salt of the organic acid A; and
   separating off precipitated NaCl;
   or
   (iii) reacting a hydrochloride salt of a N-substituted aminopolysiloxane to be obtained as a hydrosalt of an organic acid, in solution in the lower alcohol, with a sodium alkoxide of the lower alcohol, to obtain the N-substituted aminopolysiloxane as a free amine;
   separating off precipitated NaCl; and
   reacting the resultant free amine with the organic acid A;
   and
   recovering a solution of the hydrosalt of the organic acid A of the N-substituted aminopolysiloxane in the lower alcohol.

15. The process as claimed in claim 14, wherein the organic carboxylic acid A is selected from formic acid, acetic acid, propionic acid, citric acid, oxalic acid, lactic acid and mixtures thereof.

16. The process as claimed in claim 14, wherein the lower alcohol is selected from the group consisting of methanol, ethanol, isopropanol, n-propanol, isobutanol, n-butanol, t-butanol and mixtures thereof.

17. The process as claimed in claim 14, further comprising:
   dissolving an additional stabilizer in the organic acid A and adding the solution of the additional stabilizer to the hydrosalt solution.

* * * * *